(12) United States Patent
Sandal et al.

(10) Patent No.: US 6,599,743 B2
(45) Date of Patent: Jul. 29, 2003

(54) METHOD FOR MICROPRODUCTION OF TEA PLANTS FROM LEAF EXPLANTS

(75) Inventors: Indra Sandal, Himachal Pradesh (IN); Amita Bhattacharya, Himachal Pradesh (IN); Madhu Sharma, Himachal Pradesh (IN); P. S. Ahuja, Himachal Pradesh (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/813,101

(22) Filed: Mar. 22, 2001

(65) Prior Publication Data

US 2002/0137208 A1 Sep. 26, 2002

(51) Int. Cl.$^7$ .............................. C12N 5/00; C12N 5/02
(52) U.S. Cl. ..................................... 435/430.1
(58) Field of Search ....................... 435/430.1

(56) References Cited

PUBLICATIONS

Pedroso, M.C. et al., "Direct embryo formation in leaves of *Camillia japonica*," *Plant Cell Reports*, vol. 12, pp. 639–643, Springer–Verlag, (1993).

Palni et al.. "Tissue Culture Studies in Tea (*Camellia sinensis*)," *Proc. International Sym. On Tea Science*, pp. 395–399, Shizouka, Japan, (1991).

San–Jose, M.C. et al., "Regeneration of Camellia plantlets from leaf explant cultures by embryogenesis and caulogenesis," *Scientia Horticulturae*, vol. 54, pp. 303–315, Elsvier Science Publishers, Amsterdam Netherlands, (1993).

San–Jose, M.C. et al., "Adventious shoot regeneration from in vitro leaves of adult *Camellia reticulata*," *Scientia Horticulturae*, vol. 67, pp. 677–683, Elsvier Science Publishers, Amsterdam Netherlands, (1992).

Kato, M., "Somatic embryogenesis from immature leaves of in vitro grown tea shoots," *Plant Cell Reports*, vol. 15, pp. 920–923, Springer–Verlag, (1996).

Nakamura, Y., "Effective Methods of In Vitro Propagation of Tea Plants," *Reprinted from Proceedings of the International Symposium on Recent Development in Tea Production*, pp. 63–75, (1988).

Nakamura, Y. "Effects of Origin of Explants of Differentation of Root and Its Varietal Difference in Tissue Culture of Tea Plants," *Shizouka Tea Experimental Station*, vol. 62, pp. 1–8, (1995).

*Primary Examiner*—Bruce R. Campell
*Assistant Examiner*—Susan B. McCormick
(74) *Attorney, Agent, or Firm*—Foley & Lardner

(57) ABSTRACT

The present invention relates to novel method for micropropagation of tea plants from explants obtained from completely folded, half opened or fully expanded leaves via callus phase, by culturing the explants on different media.

33 Claims, 4 Drawing Sheets

(4 of 4 Drawing Sheet(s) Filed in Color)

Fig.6A
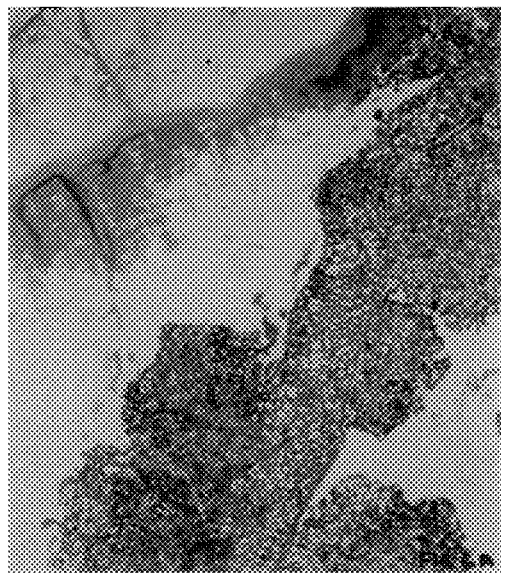
Fig.6B
Fig.6C
Fig.6D
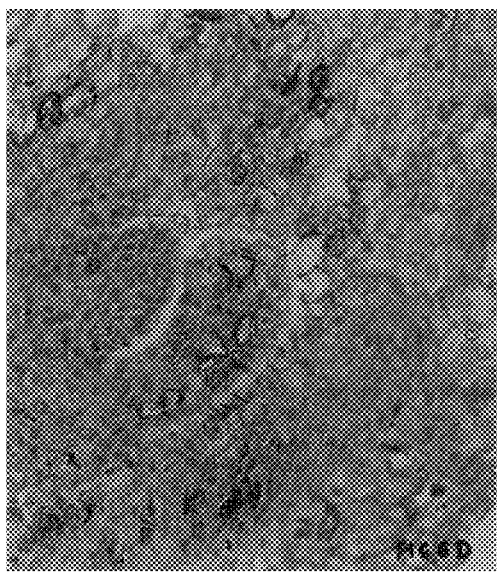
FIG.6

US 6,599,743 B2

METHOD FOR MICROPRODUCTION OF TEA PLANTS FROM LEAF EXPLANTS

FIELD OF THE INVENTION

The present invention relates to an efficient method for micropropagation of tea plants (*Camellia sinensis*) using explants excised from leaves.

BACKGROUND AND PRIOR ART REFERENCES

Tea is a popular caffeine containing beverage with anti-cancerous properties (Jankun et al. Why drinking green tea could prevent cancer, Nature 5:561; 1997). Although the genus Camellia has many species, only *C. sinensis* (L.) O. Kuntze or tea and its different cultivars are commercially important (Barua D. N. ed. Science and practice in tea culture, Tea Research Association Calcutta; 53–68; 1989).

Tea cultivation is not only an important employment generator but is also a major foreign exchange earner in all the tea growing areas of the world (Wilson, K. C. Botany and Plant Improvement in Wilson R. C., ed. Coffea Cocoa and Tea. CABI Publishing, Wallingford, UK: 167–173; 1999). However, the total production of tea is not sufficient enough to meet the demands of the domestic and the world markets (Kabra, G. D. Tea statistics for 1999 in Tea time, Vol VIII, No. 3 September–November 99, 30–31; 1999). The yield and quality of tea is further reduced by different biotic (fungi, pests and viruses) and abiotic (frost, hail, chilling, drought, nutritional deficiencies etc.) stresses (Wilson, K. C. Botany and Plant Improvement in Wilson R. C., ed. Coffea, Cocoa and Tea. CABI Publishing, Wallingford, UK: 167–173; 1999).

Tea actually being a woody tree species has a long life cycle coupled with a high degree of self incompatibility and inbreeding depression (Barua, D. N. The tea plant of commerce in Barua, D. N., ed. Science and practice in tea culture, Tea Research Association Calcutta; 53–68; 1989) that generally limit the production of high yielding but superior and stress resistant tea plants through conventional breeding methods. Therefore, application of biotechnological means would be an effective and alternative approach. However, an efficient as well as reproducible regeneration protocol is the most important pre-requisite for any biotechnological application.

The most severe problem in tea is the blister blight disease because it afflicts the young leaves and shoots that are used for making tea as a result of which 50% loss in yield is incurred. Therefore, resistance to blister blight is urgently required to compensate for this loss. Some clones have been identified which are high yielding as well as of high quality but these are susceptible to blister blight disease and hence require biotechnological improvement through homogenous tissues like leaf explants because heterogenous tissues like cotyledon explants would result in genetic segregation and loss of the desirable character of high yield and good quality. Therefore, the existing protocols involving heterogenous tissues like cotyledon explants is of no use with respect to the above objective and there is an urgent need to develop methods for micropropagation using homogenous tissues. Regeneration from leaf explants are maximally preferred because:

(i) leaf explants are homogenous.
(ii) leaves have chloroplast DNA that have extremely high copy number and thus the level of expression can be amplified by several folds if leaves are used during genetic manipulations like development of transgenics or somatic hybrids.
(iii) leaves offer larger surface area for application of any genetic manipulation techniques.
(iv) leaves are the major commercial source of made tea sold in the market.
(v) leaves provide an abundant supply of starting material
(vi) using leaves as explants will not hamper the general well being and growth of the plant.

Biotechnological crop improvement either through somatic hybridization or through transgenic technology generally requires regeneration via a callus phase provided there is no creation of somaclonal variants during the regeneration process. Since tea has a long life span, chances of chromosomal variability in the callus phase is low as compared to that of fast growing herbaceous plants. Therefore, an efficient indirect method for the micropropagation of tea plants using leaf explants via callus phase has been developed. The regeneration ability of woody plants is difficult and more so if either leaf explants are used or if the plants are very old trees of about 50 years or more.

Leaf explants have been used in other ornamental species of Camellia i. e. *C. japonica* and *C. reticulata* by (Sanjose and Vieitez, A. M. Adventitious shoot regeneration from in vitro leaves of adult *Camellia reticulata*, J.Hort.Sci. 67: 677–683; 1992; Sanjose, M. C. and Vieitz, A. M. Regeneration of Camellia plantlets from leaf explant cultures by embryogenesis and caulogenesis. Sci.Horti.54: 303–315; 1993; Pedroso, M. C. and Pais, M. S. Direct embryo formation in leaves of *C. japonica* L. plant Cell Rep. 12: 639–643; 1993) for generating plants via somatic embryogenesis or adventitious shoot bud formation via callus phase but either the conversion frequency was low (4–6%) or rooting was poor. Moreover, these are all ornamental species. However, there is no report on a method of plant regeneration from leaf explants for adventitious shoot bud formation through callus in *C. sinensis* i.e. the commercial Camellia or tea.

Attempts were first made in 1984 by Nakamura Y.(Effective methods of in vitro propagation of tea plant. Proc. Internat. Symp. On Recent Development in Tea Production, Taiwan Republic of China, 1984: 63–74 pp) for developing regeneration protocol from leaf explants wherein callus was obtained on Nitsch & Nitsch's medium (Nitsch, J. P. and Nitsch C., Haploid plants from pollen grains. Sci. (Washington), 163; 85–87; (1969) and Gamborg's medium (Gamborg, O. L., Miller, R. A. and Ojima, K. Nutrient requirements of suspension cultures of soyabean root cells. Experimental Cell Research 50: 151–58; 1968) supplemented with an auxin 2,4-Dichlorophenoxy acetic acid. The drawback of the protocol is that he failed to obtain morphogenesis or adventitious shoot bud formation. Again in 1985, Nakamura (Nakamura, Y. Effects of origin of explants on differentiation of root and its varietal difference in tissue culture of tea plants. Shizuoka Tea Experimental Station 62: 1–8; 1985) and Palni, Sood, Chand. Sharma, Rao and Jain (Palni, L. M. S. Sood, A., Chand, G., Sharma, M., Rao, D. V., Jain, N. K. Tissue culture studies in tea. Proc. International Sym. On Tea Science, Shizuoka, Japan, 395–399; 1991) attempted plant regeneration from leaf explants through callus phase wherein although he obtained rhizogenesis from the leaf callus but failed to regenerate plants from such rhizogenic calli. Thereafter, there was no report on plant regeneration from leaf explants until in 1996 wherein Kato,(Kato, M. Somatic embryogenesis from immature leaves of in vitro grown tea shoots. Plant Cell Rep.

15: 920–926; 1996) obtained a few plants from somatic embryos derived from leaf explants of in vitro grown plants on Murashige and Skoog medium (Murashige T. and Skoog F. A revised medium for rapid growth and bioassays with tobacco tissue cultures. Physiol. Plant. 15: 473–497; 1962) medium supplemented with 0.5 mg/l 2,4-Dichlorophenoxy acetic acid in liquid and 5 mg/l in 0.8% agar solidified medium. Yet, the major drawbacks of Kato's protocol are as follows:

(i) The percent of explant response with respect to induction of somatic embryo is very low (6%).

(ii) The donor plants are seedlings leading to genetic variations in the progenies.

(iii) The frequency of somatic embryo conversion into plants is very poor i. e. 7.1%.

(iv) The embryos induced were confined to specific regions of the leaf and not from all over the leaf surface rendering them unsuitable for transgenic studies.

(v) Does not involve a system for culturing leaf explants from mature selected bushes with elite characters rather it involves development of embryogenic calli from leaf explants of seedlings.

(vi) Seedlings represent heterogenous population whereas, explants collected from selected mature trees represent elite characters because they are propagated through clonal or vegetative means.

Different media were used for different steps like embryo induction, secondary embryogenesis and embryo germination Thus, there is a need in the prior art to provide an efficient micropropagation method for developing healthy tea plants.

OBJECTS OF THE INVENTION

The main objective of the present invention is to develop healthy tea plants from explants obtained from leaves, using an efficient method for micropropagation of tea via callus phase.

Another object of the present invention is to introduce foreign genes of interest into leaf explants and develop large number of genetically modified plants both directly through biolistic gun or indirectly Agrobacterium mediation.

Still another object of the present invention is to develop regeneration protocol for leaf derived protoplasts and somatic hybridization.

Yet another object of the present invention is to introduce genes of interest into protoplasts and study their expression.

Yet another object of the present invention to facilitate the uptake of virus particles.

SUMMARY OF THE INVENTION

Accordingly, the invention provides a novel method micropropagation for development of large number of viable and healthy plants using explants from leaves.

DETAILED DESCRIPTION OF THE INVENTION

Accordingly, the present invention provides an efficient method for micropropagation of tea (*Camellia sinensis*) plants, said method comprising the steps of:

(a) excising an explant from a completely folded, half opened or fully expanded leaf from in vitro raised tea plants, (b) culturing the ex-plant for callus induction in a first medium (Murashige T. and Skoog F. A revised medium for rapid growth and bioassays with tobacco tissue cultures. Physiol. Plant. 15: 473–497; 1962), said medium being 0.8% agar solidified basal Murashige and Skoog's medium supplemented with vitamins, 1 to 3 mg/l glycine, 2.5 to 10.0 mg/l 2,4-Dichlorophenoxy acetic acid and 1.3% sucrose for a period of 4–6 weeks at a temperature between 20° C. to 40° C., in the presence of white cool light of at least 52 $\mu$gmolm$^{-2}$s$^{-1}$ with 16 hour photo-period, (c) transferring the calli to a second medium for rhizogenesis, said medium being a 0.8% agar solidified basal MS medium supplemented with cytokinins such as 0.5 to 8 mg/l (a) 6-Benzyl amino purine and auxins such as 0.1 to 0.8 mg/l Indole-3-Butyric acid or Indole-3-acetic acid for a period of at least 6 to 10 weeks, (b) transferring the rhizogenic calli to a third medium for shoot bud initiation, said medium being an auxin free medium and containing 0.5 to 8 mg/l 6-Benzyl amino purine for a period of 4–10 weeks, (c) transferring and culturing the shoot buds to a fourth multiplication medium, said medium being a liquid medium supplemented 5 $\mu$m Thidiazuron (Sandal I., Bhattacharya A. and Ahuja P. S. 2001. An efficient liquid culture system for tea shoot proliferation. Plant Cell Tiss. Organ Culture 00. 1–6), for 4 to 6 weeks to obtain rooted shoots, (d) the cut ends of 3 cm. long shoots, are treated with Indole-3-butyric acid for a period of 20–30 minutes and culturing the shoots in jars containing sand and soil mix in the ratio 1:1 for 60–75 days, and (e) growing the rooted shoots in fields to obtain viable and healthy tea plants.

In an embodiment, the ex-plants are selected from tea cultivars such as Chinary, Assamica and Cambod. In the invention, the ex-plants are excised from fresh completely folded, half opened or fully expanded leaves. In fact, the overall or entire surface of the leaf explants were found responsive when leaf explants were excised from the leaves of the second and third position from the shoot tip. The leaves may be selected from any tea cultivar growing under in vivo and/or in vitro conditions. In other words, the explants are excised from the first leaf or the completely folded leaf most closely attached to the apical bud. The leaf explants from any cultivar may be used. Indirect shoot bud may be regenerated via callus formation by inducing meristematic activity in the leaf explants.

The leaves from the tea cultivars are first cleaned in a solution containing Bavistin (0.1%) and streptomycin (0.05%), washed in Tween 20 and surface sterilized in 0.01% (w/v) mercuric chloride solution containing a drop of liquid detergent followed by thorough washings in sterile distilled water. The surface sterilized explants are then cultured as described according to the method of the invention.

In an embodiment, the first medium, being the callus induction medium is supplemented with vitamins like thiamine-HCl 0.05 to 2 mg/l, pyridoxine-HCl 0.25 to 1.5 mg/l and nictotinic acid 0.25 to 1.5 mg/l. The ex-plants are placed in this first medium and incubated at 20 to 40° C. in the presence of cool fluorescent light of 52 $\mu$molm$^{-2}$s$^{-1}$ with 16 hour photoperiod, for a period of at least 6–10 weeks, preferably, for 6 weeks.

In an embodiment, for rhizogenesis, the calli obtained in step (b) are transferred to a second medium which is a 0.8% agar solidified basal MS medium supplemented with 0.5 to 8 mg/l 6 Benzyl amino purine and auxins such as Indole-3-acetic acid or Indole-3-butyric acid (0.1 to 0.8 mg/l). The calli are placed in the second medium for a period of 4 to 6 weeks, preferably for 6 weeks. The pH of the medium was 5.6 to 7.6. The culture was incubated at 24 to 30° C. in the presence of cool fluorescent light of 52 $\mu$molm$^{-2}$ s$^{-1}$ and 16 hour photoperiod.

The calli are placed in the third medium for rhizogenesis for a period preferably of 4 to 6 weeks.

In an embodiment, the shoot buds obtained from step (d) after 6 weeks were excised (about 3 cms) and allowed to grow on a fourth medium which is a 0.8% agar solidified basal MS medium supplemented with 3% sucrose and 5 $\mu$M Thidiazuron and 10 $\mu$M Naphthalene acetic acid till they grew to 2.0 cm. The medium is supplemented with auxins and cytokinins.

In an embodiment, the microshoots thus obtained were then multiplied in static 20 ml liquid medium containing 3% sucrose and 5 $\mu$M Thidiazuron.

In an embodiment the auxins used as plant growth regulators for callus formation and rhizogenesis were selected from Indole-3-Butyric acid, Indole-3 acetic acid, Naphthalene acetic acid and 2,4-Dichlorophenoxy acetic acid.

In yet another embodiment the cytokinins used as plant growth regulator for rhizogenesis were selected from 6 Benzyl amino purine, kinetin and Thiadiozuron but preferably on 6 Benzyl amino purine.

In still another embodiment the responsive rhizogenic calli need to be transferred to auxin free medium for shoot bud formation after 4 to 10 weeks but preferably after 4 weeks.

In yet another embodiment it is necessary to culture the materials specifically in 9.0 cm petri-dishes containing 25 ml medium (pH 5.6).

In another embodiment culture media are maintained at pH range of 5.6 to 6.6.

In still another embodiment the micro-shoots were rooted by treating the cut ends with 5 mg/l Indole butyric acid and planting in sterile sand: soil (1:1) mix in pots covered with inverted jars under culture lab conditions for 8 weeks and then transferring rooted shoots to plastic pots under ambient temperatures.

In yet another embodiment of the present invention leaf explants of either in vitro or ex vitro raised selected plants of hybrid cultivars used as in above were subjected to the following steps:

i) completely folded, half opened or fully explanded leaf explants of in vitro raised cultures of any clone on (0.8%) agar solidified basal MS medium supplemented with 3% sucrose and 6 Benzyl amino purine (0.5 to 8.0 mg/l) and Indole-3-butyric acid (0.1 to 0.8 mg/l);

ii) the explant were placed on agar (0.8 to 1.0%) solidified MS medium supplemented with 2–5% sucrose and 2.5, 5.0, 7.5 or 10.0 mg/l of either 2,4-Dichlorophenoxy acetic acid, Indole-3-acetic acid, Indole-3-butyric acid singly or in combination with 6 Benzyl amino purine or Thidiazuron (0,0.1, 0.2 mg/l) in petri dishes containing agar gelled 25 ml basal MS medium and incubated at 25±2° C. with cool fluorescent light (52 $\mu$molm$^{-2}$s$^{-1}$) for callus induction.

iii) For rhizogenesis, the cultures obtained from step were transferred to (0.8% agar solidified basal MS medium supplemented with 3% sucrose and 6 Benzyl amino purine or Thidiazuron (0.5 to 8.0 mg/l) in combination with Indole-3-acetic acid, Indole-3-butyric acid (0.1 to 0.8 mg/l).

iv) For adventitious shoot bud formation, the rhizogenic callus cultures obtained from step (iii) were transferred to (0.8%) agar solidified basal MS medium supplemented with 6 Benzyl amino purine (0.5 to 8.0 mg/l) and 3% sucrose.

v) The shoot buds obtained from step (iv) after 6 weeks were excised and allowed to grow on (0.8%) agar solidified basal MS medium supplemented with 3% sucrose and 5 $\mu$M thidiazuron and 10 $\mu$M Naphthalene acetic acid till they grew to 2.0 cm.

vi) The microshoot thus obtained were then multiplied on static 20 ml liquid medium containing 3% sucrose and 5 $\mu$M Thidiazuron.

vii) The micro-shoots were rooted by treating the cut ends with 5 mg/l IBA and planting in sterile sand: soil (1:1) mix in pots covered with inverted jars under culture lab conditions for 8 weeks and then transferring the rooted shoots to plastic pots under ambient temperature.

It is the applicants' finding that presence of 2,4-Dichlorophenoxy acetic at high concentrations in the first medium is known to induce active cell division and undifferentiated growth resulting in callus formation in plant tissues. This has also been found to be true in case of tea. However, transfer of these undifferentiated masses to a medium supplemented with 6 Benzyl amino purine and Indole-3-acetic or Indole-3-Butyric acid at specific concentrations result in the development of certain meristematic pockets comprising of vascular tissues like the trachieds. These meristematic pockets eventually develop into adventitious roots and then into adventitious shoot buds on transfer to auxin free medium containing only 6 Benzyl amino purine.

Since 1984, several workers had attempted to generate shoots from leaf explants via callus phase in tea i. e. *Camellia sinensis*. However, they have failed till date to progress beyond rhizogenic calli. The novelty of the present invention is that it was realized that auxins like 2,4-Dichlorophenoxy acetic acid or Indole-3-acetic or Indole-3-Butyric acid at certain concentrations has the potential for triggering morphogenesis towards the root pole. Therefore, it was hypothesized that if this morphogenic trigger could be diverted towards the opposite pole that is the shoot pole, it would be possible to get plants from such rhizogenic calli. Since cytokinins are known to induce shoot morphogenesis, 6 Benzyl amino purine was used and more than 30% adventitious shoot bud development could be successfully achieved in almost 100% of the explants. The invention is the first to report that development of adventitious shoot buds can be induced on rhizogenic calli derived from leaf explants.

The novel features of the invention that distinguish the invention from the prior art methods are as under:

(i) The percent of leaf explant response is high (almost 100%)

(ii) Leaf explants selected from mature tea plants (both ex vitro and in vitro) are found to respond efficiently.

(iii) The method is quite effective for clonal propagation of selected/elite clones.

(iv) The method involves callus formation which develops from all over the surface and is not localised to specific regions of the leaf surface.

(v) This method enables the production of more than 30% adventitious shoot bud formation which grow into healthy plants that can be easily multiplied or transferred to soil after rooting.

(vi) This is the first report on high frequency plant regeneration through adventitious shoot bud formation from callus obtained from leaf explants in contrast to all the previous reports which have failed to achieve plants from leaf explants through adventitious buds.

(vii) This method offers a potential for higher frequency of genetic transformation as compared to the protocol suggested by Kato (1996). This is because the protocol offers the potential for single cells that are genetically transformed to have much higher chances of multiplying and making the transformant successful as compared to the low frequency of Genetically transformed somatic embryos that are due to the region specific induction.

The patent or application file contains at least one drawing executed in color. Copies of this patent or patent application publication with color drawings will be provided by the U.S. Patent and Trademark Office upon request and payment of the necessary fee.

The invention is further illustrate by the following diagrams wherein

FIGS. 6A–6D represents cell studies wherein the callus development occurred from all around the vascular bundle of the leaf tissue (FIG. 6A).

Figure 1:
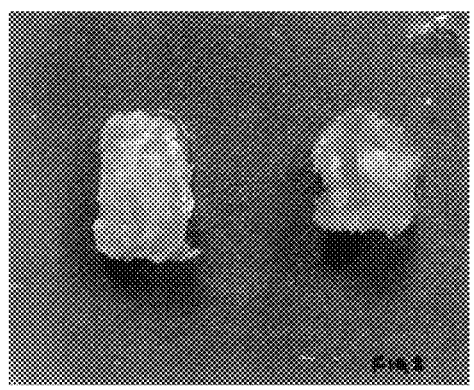
FIG. 1 represents leaf explants that respond maximally.
Figure 2:
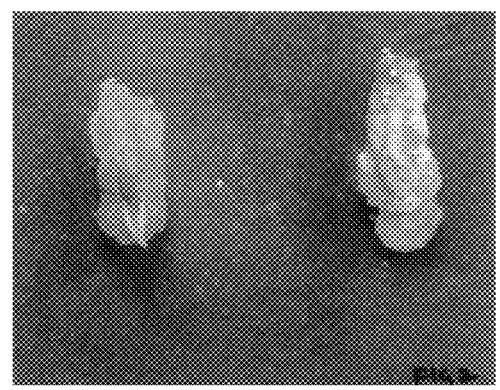
FIG. 2 represents induction of callus on the leaf explants and proliferation of callus all over the leaf explants.
Figure 3:
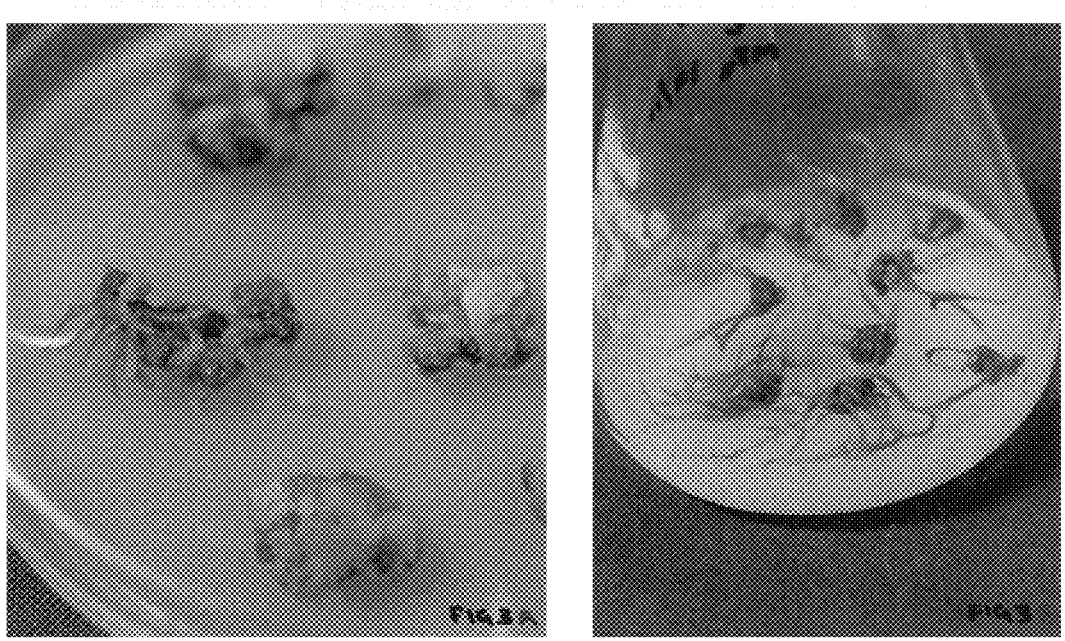
FIGS. 3A–3B represents rhizogenesis from all over the callus derived from the leaf explants. Rhizogenesis represents the turning point where the path of undifferentiated growth to a path of morphogenesis.
Figure 4:
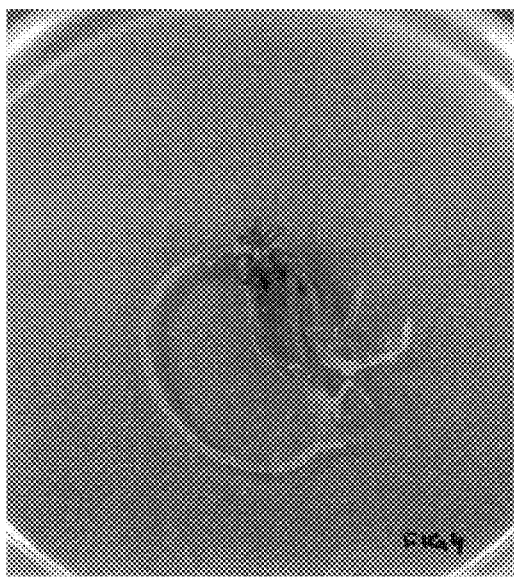
FIG. 4 represents adventitious shoot bud formation from the rhizogenic calli.
Figure 5:
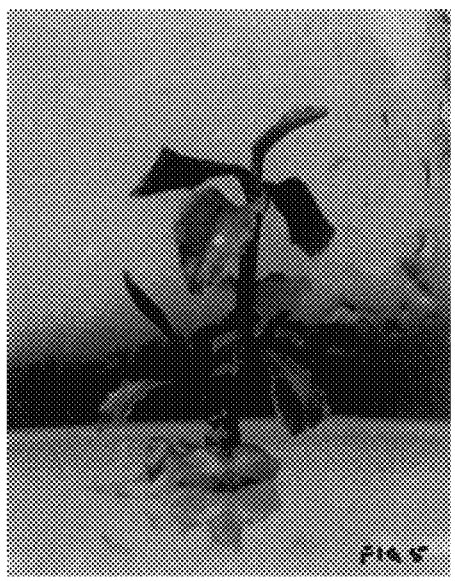
FIG. 5 represents the microshoots developed from the adventitious shoot buds and root initiation from microshoots.

Although the callus cells indicated no vascular elements when they were cultured on CIM medium supplemented with 2,4-D, yet development of individual or scattered groups of tracheids were observed when calli were transferred MS1 or MS2 medium indicating the initiation of meristemoid development (FIG. 6B). After 2 weeks of culture on MS1/MS2 medium however, development of these meristemoids were followed by meristematic structures. Finally after 4 weeks of culture these meristematic structures developed into cluster of 5–8 roots (FIG. 6C). After 4 weeks of transfer to MS3 medium, some of the meristemoids developed into shoot buds (FIG. 6D).

For better understanding of the invention, following examples are provided, which should not be construed as limitations on the inventive scope.

EXAMPLE 1

Any leaf ranging from completely folded, half opened or fully expanded leaf plants of in vitro raised plants of the important cultivars (Chinary, Assamica and Cambod) were the responsive explants when they were placed on (0.8%) agar solidified basal MS medium supplemented with 3% sucrose and 2.5 to 10.0 mg/l 2,4-D (pH 5.6±0.2) for 6 to 10 weeks at a temperature of 25±2° C. and a photoperiod of 16 h under cool fluorescent light of 52 $\mu$mol m$^{-2}$s$^{-1}$. The callus thus developed after 6–10 weeks was transferred to (0.8%) agar solidified basal MS medium supplemented with 3% sucrose and 0.5 to 8.0 mg/l 6 Benzyl amino purine and 0.1 to 0.8 mg/l Indole-3-Butyric acid for rhizogenesis or adventitious root formation. After 4–10 weeks, the rhizogenic callus was transferred to (0.8%) agar solidified basal MS medium supplemented with 3% sucrose and 0.5 to 8.0 mg/l 6 Benzyl amino purine for adventitious shoot bud formation. The adventitious shoot buds were excised and allowed to grow into 1.5–2.0 cm long microshoots on (0.8%) agar solidified basal MS medium supplemented with 3% sucrose and 0.5 to 8.0 mg/l 6 Benzyl amino purine and 0.1 to 0.8 mg/l Indole-3-Butyric acid and were then multiplied in static 20 ml liquid MS medium supplemented with 3% sucrose and 5 $\mu$M Thidiazuron for 6 weeks. Cut end of each of the 3.0 cm long microshoot was treated with Indole-3-Butyric acid (5.0 mg/l) for 20–30 minutes and planted in sand: soil mix (1:1) for 60–75 days and finally the rooted plantlets were transferred to plastic pots.

EXAMPLE-2

Any leaf ranging from completely folded, half opened or fully expanded leaf explants from 50 years old selected plants of the important cultivars (Chinary, Assamica and Cambod) from the Institute of Himalayan Bioresource Technology's Experimental farm, Banuri, Palampur (36° N. and 78.18° E. and 1290 m above sea level) were used as explants. The leaves were cleaned carefully with a sable hair brush and liquid detergent, washed in Tween 20 containing Bavistin (0.1%) and streptomycin (0.05%) and surface sterilized in 0.01% mercuric chloride solution containing a drop of liquid detergent followed by a thorough rinse in distilled water. The sterilized explants were cultured similarly as per details given in the above mentioned protocol.

EXAMPLE-3

Any leaf ranging from completely folded, half opened or fully expanded leaf explants of in vitro raised plants of other hybrid cultivars like Tocklai Variety 1 were the responsive explants when they were placed on (0.8%) agar solidified basal MS medium supplemented with 3% sucrose and 2.5 to 10.0 mg/l 2,4-D (pH 5.6±0.2) for 6–10 weeks at a temperature of 25±2° C. and a photoperiod of 16 h under cool fluorescent light of 52 $\mu$mol m$^{-2}$s$^{-1}$. The callus thus developed after 6–10 weeks was transferred to (0.8%) agar solidified basal MS medium supplemented with 3% sucrose and 0.5 to 8.0 mg/l 6 Benzyl amino purine and 0.1 to 0.8 mg/l Indole-3-Butyric acid for rhizogenesis or adventitious root formation. After 6–10 weeks, the rhizogenic callus was transferred to (0.8%) agar solidified basal MS medium supplemented with 3% sucrose and 0.5 to 8.0 mg/l 6 Benzyl amino purine for adventitious shoot bud formation. The shoots obtained from adventitious shoot buds were multiplied in static 20 ml liquid MS medium supplemented with 3% sucrose and 5 $\mu$M Thidiazuron for 6 weeks. Cut end of each of the 3.0 cm long microshoot was treated with Indole-3-Butyric acid (5.0 mg/l) for 20–30 minutes and planted in sand: soil mix (1:1) for 60–75 days and finally the rooted plantlets were transferred to plastic pots.

The main advantages of the present invention are:

(1) Healthy plants can be regenerated from truly homogenous leaf tissue.
(2) The present invention can be used to generate blister blight resistant plants
(3) The method can also be used for protoplast culture and somatic hybridization.
(4) The method can be applied for chloroplast transformation through direct delivery methods
(5) The method for developing high frequency transgenics is possible as rapid multiplication of single cell transformants can occur via callus phase as compared to direct regeneration from the leaf tissue without intervening callus.
(6) Frequency of transformants through this method will be much higher than existing protocols as the development of callus is from all over the leaf surface as compared to the region specific induction of somatic embryos in previous reports.

(7) The present invention can be used for developing methods for the introduction of genes of interest into protoplasts and for the study of their expression.

(8) The present invention can be used to facilitate the uptake of virus particles.

(9) The present invention can be used to produce plants expressing maternally inherited traits like cytoplasmic male sterility, tolerance to herbicides like atrazine.

(10) The use of 25 ml medium in petri-dish as compared to the use of 50–100 ml medium in pre-existing methods makes it a cost effective process.

What is claimed is:

1. A method for micropropagation of tea plants, comprising culturing tea leaf explants on callus induction medium comprising auxin, vitamins, and glycine until calli are induced, subculturing the induced calli on medium comprising auxin and cytokinin to induce rhizogenesis, transferring the rhizogenic calli to auxin-free shoot bud initiation medium comprising cytokinin until shoot buds are formed, transferring shoot buds to a fourth medium to obtain shoots and excising shoots for rooted soil growth.

2. The method of claim 1, wherein said explants comprise tea cultivars Chinary, Assamica, and Cambod.

3. The method of claim 1, wherein said explants comprise leaves most closely attached to the apical bud.

4. The method of claim 1, wherein said explants are excised from the second and third leaves from the shoot tip.

5. The method of claim 1, wherein said rhizogenic calli are cultured on said shoot induction medium for a period of 4–10 weeks.

6. The method of claim 1, wherein said auxin is selected from the group consisting of indole-3-butyric acid, indole-3-acetic acid, naphthaleneacetic acid, and 2,4-dichlorophenoxyacetic acid.

7. The method of claim 1, wherein said cytokinin is selected from the group consisting of 6-benzylaminopurine, kinetin, and thiadiazuron.

8. The method of claim 1, whereby said explants and said calli are grown under cool fluorescent light.

9. The method of claim 3, wherein said leaves are completely folded, half openend, or fully expanded leaves.

10. The method of claim 1, wherein said vitamins comprise thiamine-HCl, pyridoxine-HCl, and nicotinic acid.

11. The method of claim 10, wherein the concentration range of thiamine-HCl is 0.05–2.0 mg/l.

12. The method of claim 10, wherein the concentration range of pyridoxine-HCl is 0.25–1.5 mg/l.

13. The method of claim 10, wherein the concentration range of nicotinic acid is 0.25–1.5 mg/l.

14. The method of claim 6, wherein said auxin is 2,4-dichlorophenoxyacetic acid.

15. The method of claim 14, wherein the concentration range of 2,4-dichlorophenoxyacetic acid is 2.5–10 mg/l.

16. The method of claim 15, wherein said concentration is 5.0 mg/l.

17. The method of claim 1, wherein said explant is cultured in the callus induction medium for a period of 6–10 weeks.

18. The method of claim 1, wherein said cytokinin is 6-benzylaminopurine.

19. The method of claim 18, wherein the concentration range of 6-benzylaminopurine is 0.5–8.0 mg/l.

20. The method of claim 19, wherein said concentration is 2.0 mg/l.

21. The method of claim 1, wherein said auxin is selected from the group consisting of indole-3-butyric acid and indole-3-acetic acid.

22. The method of claim 21, wherein the concentration range of indole-3-butyric acid is 0.1–0.8 mg/l.

23. The method of claim 22, wherein said concentration is 0.2 mg/l.

24. The method of claim 21, wherein the concentration range of indole-3-acetic acid is 0.1–0.8 mg/l.

25. The method of claim 24, wherein said concentration is 0.2 mg/l.

26. The method of claim 7, wherein said cytokinin is 6-benzylaminopurine.

27. The method of claim 26, wherein the concentration range of 6-benzylaminopurine is 0.5–8.0 mg/l.

28. The method of claim 27, wherein said concentration is 2.0 mg/l.

29. The method of claim 8, wherein the intensity of said light is 52 $\mu$Em$^2$s$^{-1}$.

30. The method of claim 1, wherein the length of said excised shoot is at least 3.0 cm.

31. The method of claim 30, wherein the end of said excised shoot is treated with indole-3-butyric acid.

32. The method of claim 31, wherein the concentration of indole-3-butyric acid is 5.0 mg/l.

33. The method of claim 31, wherein said excised shoot is treated with indole-3-butyric acid for a period of 20–30 minutes.

* * * * *